(12) United States Patent
Johnson

(10) Patent No.: US 11,197,611 B2
(45) Date of Patent: Dec. 14, 2021

(54) SYSTEMS AND METHODS FOR DETERMINING SPATIAL LOCATIONS OF PATIENT DATA GATHERING DEVICES

(71) Applicant: ZOLL Medical Corporation, Chelmsford, MA (US)

(72) Inventor: Guy R Johnson, Wilton, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 202 days.

(21) Appl. No.: 16/163,912

(22) Filed: Oct. 18, 2018

(65) Prior Publication Data

US 2019/0117069 A1    Apr. 25, 2019

Related U.S. Application Data

(63) Continuation of application No. 15/611,933, filed on Jun. 2, 2017, now Pat. No. 10,143,375, which is a continuation of application No. 14/158,027, filed on Jan. 17, 2014, now Pat. No. 9,693,691.

(60) Provisional application No. 61/754,409, filed on Jan. 18, 2013.

(51) Int. Cl.
| A61B 5/00 | (2006.01) |
| A61B 5/11 | (2006.01) |
| G16H 40/67 | (2018.01) |
| G16Z 99/00 | (2019.01) |

(52) U.S. Cl.
CPC .......... *A61B 5/0022* (2013.01); *A61B 5/1112* (2013.01); *G16H 40/67* (2018.01); *G16Z 99/00* (2019.02)

(58) Field of Classification Search
CPC ..................................................... A61B 5/022

USPC ......................................................... 701/454
See application file for complete search history.

(56) References Cited

U.S. PATENT DOCUMENTS

| 3,747,605 A * | 7/1973 | Cook .................... A61N 1/3937 607/8 |
| 6,246,907 B1 * | 6/2001 | Lin ........................ A61B 5/352 607/5 |
| 6,289,243 B1 * | 9/2001 | Lin ...................... A61N 1/3904 607/5 |
| 6,747,556 B2 | 6/2004 | Medema et al. |

(Continued)

FOREIGN PATENT DOCUMENTS

| WO | 2004074777 | 9/2004 |
| WO | 2012095829 | 7/2012 |

*Primary Examiner* — Jean Paul Cass
(74) *Attorney, Agent, or Firm* — ZOLL Medical Corporation

(57) ABSTRACT

An example of a mobile computing device for managing medical equipment includes a display and a processor, a memory, and associated circuitry, the processor configured to receive patient data gathering device location information for a plurality of patient data gathering devices, the patient data gathering device location information being indicative of one or more patient data gathering device locations in an assigned monitoring area corresponding to the mobile computing device, control the display to provide the patient data gathering device location information, capture a user selection of at least one patient data gathering device of the plurality of patient data gathering devices based on the provided patient data gathering device location information, and provide patient data gathering device information based on the user selection.

58 Claims, 5 Drawing Sheets

(56) References Cited

U.S. PATENT DOCUMENTS

| | | |
|---|---|---|
| 6,957,102 B2 | 10/2005 | Silver et al. |
| 7,231,258 B2 | 6/2007 | Moore et al. |
| 7,539,533 B2 | 5/2009 | Tran |
| 7,605,696 B2 | 10/2009 | Quatro |
| 7,624,027 B1 | 11/2009 | Stern et al. |
| 7,751,971 B2 | 7/2010 | Chang et al. |
| 8,038,593 B2 | 10/2011 | Friedman et al. |
| 8,139,945 B1 | 3/2012 | Amir et al. |
| 8,261,083 B2 * | 9/2012 | Nakamura ............ G01C 21/32 |
| | | 713/176 |
| 8,314,683 B2 | 11/2012 | Pfeffer |
| 8,362,942 B2 | 1/2013 | Mcneill et al. |
| 8,633,806 B2 | 1/2014 | Amir |
| 8,779,965 B2 | 7/2014 | Sentelle et al. |
| 8,923,805 B2 | 12/2014 | Single |
| 8,924,864 B2 | 12/2014 | Mariotti et al. |
| 9,000,930 B2 | 4/2015 | Pelland et al. |
| 9,026,147 B2 | 5/2015 | Galvin et al. |
| 9,063,232 B2 | 6/2015 | Mcneill et al. |
| 9,092,964 B1 | 7/2015 | Chan et al. |
| 9,219,984 B1 | 12/2015 | Amir et al. |
| 9,232,040 B2 | 1/2016 | Barash et al. |
| 9,242,109 B2 | 1/2016 | Gordon et al. |
| 9,298,958 B1 | 3/2016 | Amir |
| 9,443,415 B2 | 9/2016 | Nepo |
| 9,549,683 B2 | 1/2017 | Jia et al. |
| 9,656,092 B2 | 5/2017 | Golden |
| 2003/0036683 A1 | 2/2003 | Kehr et al. |
| 2003/0109901 A1 * | 6/2003 | Greatbatch ............ A61B 5/287 |
| | | 607/9 |
| 2003/0109904 A1 * | 6/2003 | Silver ................ A61N 1/37211 |
| | | 607/59 |
| 2005/0022274 A1 * | 1/2005 | Campbell ............... G16Z 99/00 |
| | | 604/131 |
| 2007/0038138 A1 * | 2/2007 | Gill ...................... A61N 1/3702 |
| | | 600/513 |
| 2007/0139191 A1 * | 6/2007 | Quatro ................... G06Q 10/08 |
| | | 340/539.13 |
| 2007/0210923 A1 * | 9/2007 | Butler ................ G06K 19/0723 |
| | | 340/572.8 |
| 2007/0229350 A1 | 10/2007 | Scalisi et al. |
| 2007/0273504 A1 * | 11/2007 | Tran ...................... A61B 5/282 |
| | | 340/539.12 |
| 2008/0121690 A1 * | 5/2008 | Carani ................... G06Q 30/02 |
| | | 235/376 |
| 2008/0122656 A1 * | 5/2008 | Carani ................... G07C 5/008 |
| | | 340/995.28 |
| 2008/0122691 A1 * | 5/2008 | Carani ................... H04W 4/02 |
| | | 342/357.48 |
| 2008/0125964 A1 * | 5/2008 | Carani ................... G06Q 10/08 |
| | | 701/408 |
| 2008/0125965 A1 * | 5/2008 | Carani ..................... G08G 1/20 |
| | | 701/408 |
| 2008/0174485 A1 * | 7/2008 | Carani ................... G06Q 10/08 |
| | | 342/357.46 |
| 2010/0292556 A1 * | 11/2010 | Golden .................. G16H 40/67 |
| | | 600/364 |
| 2011/0117878 A1 * | 5/2011 | Barash ................. G08B 25/005 |
| | | 455/404.2 |
| 2012/0011253 A1 | 1/2012 | Friedman et al. |
| 2012/0271370 A1 * | 10/2012 | Hochhalter ........ G08B 21/0202 |
| | | 607/5 |
| 2013/0012151 A1 * | 1/2013 | Hankins ................ H04W 76/50 |
| | | 455/404.1 |
| 2013/0086469 A1 * | 4/2013 | Lundberg .......... G06F 16/24578 |
| | | 715/255 |
| 2013/0087609 A1 * | 4/2013 | Nichol .................... G06F 16/23 |
| | | 235/375 |
| 2013/0131529 A1 * | 5/2013 | Jia .......................... A61B 5/333 |
| | | 600/510 |
| 2013/0252574 A1 * | 9/2013 | Single ..................... H04W 4/90 |
| | | 455/404.2 |
| 2013/0300573 A1 | 11/2013 | Brown et al. |
| 2014/0002241 A1 | 1/2014 | Elghazzawi |
| 2014/0087762 A1 * | 3/2014 | Galvin .................. G16H 40/67 |
| | | 455/456.3 |
| 2014/0218537 A1 * | 8/2014 | Nepo ................... G08B 25/009 |
| | | 348/158 |
| 2014/0277227 A1 * | 9/2014 | Peterson ............. A61N 1/3987 |
| | | 607/7 |
| 2014/0335893 A1 * | 11/2014 | Ronen ................... G01S 5/0252 |
| | | 455/456.1 |
| 2015/0002293 A1 * | 1/2015 | Nepo ...................... A61K 9/703 |
| | | 340/539.13 |
| 2015/0137972 A1 * | 5/2015 | Nepo ..................... G08B 25/10 |
| | | 340/539.13 |
| 2015/0151769 A1 * | 6/2015 | DeSanzo ................. B61L 27/00 |
| | | 701/70 |
| 2015/0178457 A1 * | 6/2015 | Grimley ................ G06F 40/169 |
| | | 705/3 |
| 2016/0361014 A1 * | 12/2016 | Kane ..................... A61B 5/1123 |
| 2017/0100050 A1 * | 4/2017 | Jia ......................... A61B 5/316 |

* cited by examiner

SYSTEMS AND METHODS FOR DETERMINING SPATIAL LOCATIONS OF PATIENT DATA GATHERING DEVICES

CROSS-REFERENCE TO RELATED APPLICATION

This application is a continuation under 35 U.S.C. § 120 of U.S. patent application Ser. No. 15/611,933, filed on Jun. 2, 2017 and issued as U.S. Pat. No. 10,143,375, which is a continuation of U.S. patent application Ser. No. 14/158,027, filed on Jan. 17, 2014 and issued as U.S. Pat. No. 9,693,691, which claims the benefit under 35 U.S.C. § 119(e) to U.S. Provisional Patent Application No. 61/754,409, filed on Jan. 18, 2013. All subject matter set forth in the above referenced applications is hereby incorporated by reference in its entirety into the present application as if fully set forth herein.

TECHNICAL FIELD

The present invention relates to systems and methods for determining the spatial location of one or more patient data gathering devices. More specifically, the present invention relates to systems and methods for determining the spatial locations of multiple patient data gathering devices, communicably connecting nearby patient data gathering devices, and presenting the locations of the patient data gathering devices on an electronic map.

BACKGROUND

Patient data gathering devices used in emergency medical service (EMS) applications, for example, defibrillators, are typically complex and expensive. Thus, the number of devices employed in many areas is often relatively low. Nevertheless, the locations of such devices are typically tracked manually (for example, verbally or via an electronic log). Thus, it may be cumbersome to efficiently locate and redirect patient data gathering devices in certain situations, such as mass casualty situations.

Further, patient data gathering devices typically include wireless data transceivers to transmit medical information for storage in a remote medical database. However, some designs lack relatively long-range communication components (such as cellular or Wi-Fi transceivers) and in some situations, such as mass casualty situations, relatively long-range communication methods may be unavailable. In these cases, some patient data gathering devices turn to relatively short-range, device-to-device communication methods (such as near-field communications (NFC), Bluetooth, and the like) to transmit medical information. However, these devices may expend a significant amount of power by attempting to communicate with devices near the edge of their transmission range.

SUMMARY

A method for determining and presenting a spatial location of at least one patient data gathering device according to embodiments of the present invention includes receiving at least one signal from a geolocation system, analyzing the at least one signal to determine the spatial location of the at least one patient data gathering device, receiving an electronic map including the spatial location of the at least one patient data gathering device, generating a device location map by modifying the electronic map to include an icon at the spatial location of the at least one patient data gathering device, and generating a report including the device location map.

A method for determining a spatial proximity of a first patient data gathering device of a plurality of patient data gathering devices relative to second and third patient data gathering devices of the plurality of patient data gathering devices includes receiving at least one signal from a geolocation system, analyzing the at least one signal to determine the spatial location of the first patient data gathering device, receiving respective spatial locations of the second and third patient data gathering devices, and comparing the spatial location of the first patient data gathering device to the respective spatial locations of the second and third patient data gathering devices to determine a closer of the second and third patient data gathering devices to the first patient data gathering device.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
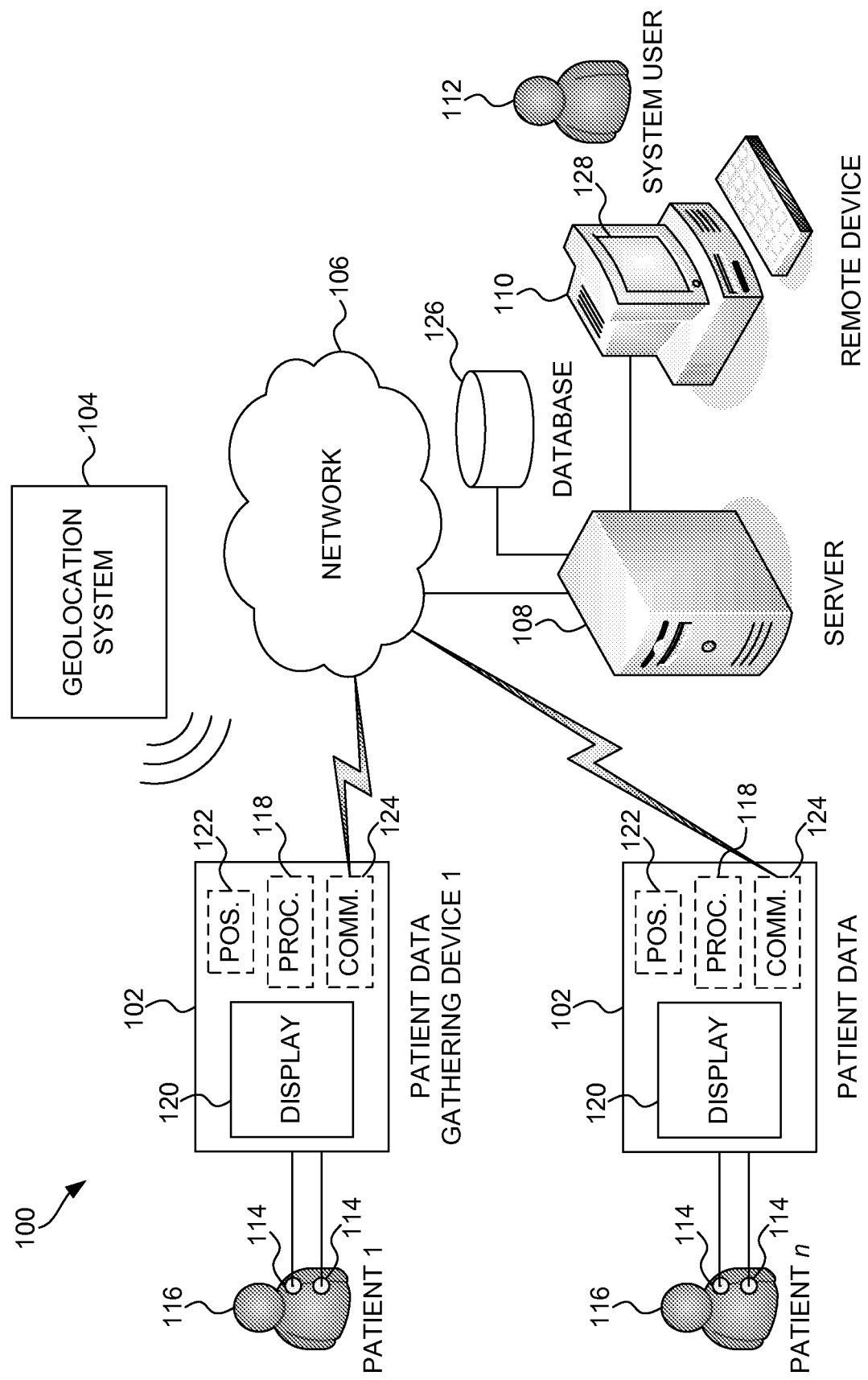
FIG. 1 illustrates a system for determining and displaying the spatial location of one or more patient data gathering devices according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates a system 100 for determining and presenting the spatial location of one or more patient data gathering devices 102. In some embodiments, such location determinations are facilitated by a remote geolocation system 104 (for example, the Global Positioning System (GPS), a cellular geolocation system, a Wi-Fi geolocation system, or the like). The patient data gathering devices 102 communicate with and transmit location information (for example, using cellular data transmissions, Wi-Fi, near-field communications (NFC), Bluetooth, and the like) to a server 108 via a network 106 (for example, the Internet or a mesh network). The server 108 incorporates the location information into a map. The server 108 transmits the map to a remote terminal or device 110 for presentation to a system user 112.

The patient data gathering devices 102 may be, for example, defibrillators (such as ZOLL® X-Series® or E-Series® devices), automatic external defibrillators (AEDs, such as ZOLL® AED Pro® devices), wearable cardioverter defibrillators (such as ZOLL® LifeVest® devices), combinations thereof, and the like. Some of the patient data gathering devices 102 may be assigned to patients (that is, currently connected to patients and gathering data), and some of the patient data gathering devices 102 may be unassigned (that is, currently disconnected from patients and not gathering data). For simplicity, the following paragraphs only provide the details for one assigned patient data gathering device 102. It is to be understood, however, that in some embodiments similar details apply to each of the different types of devices 102.

The patient data gathering device 102 receives signals from one or more sensors or electrodes 114 coupled to the patient 116. In some embodiments, a processor 118 uses such signals to monitor, detect, and/or derive or calculate various patient conditions. For example, the processor 118 may monitor, detect, an/or derive or calculate heart rate, blood pressure, temperature, respiration rate, blood oxygen level, end-tidal carbon dioxide level, pulmonary function, blood glucose level, and/or weight. In some embodiments, the patient data gathering device 102 includes a display 120 for presenting data associated with one or more of the above medical parameters. For example, the display 120 may present an electrocardiograph (ECG).

In some embodiments and as shown in FIG. 1, the patient data gathering device 102 includes a positioning device 122, such as a GPS receiver, to receive signals from the geolocation system 104. For example, the positioning device 122 may receive signals from multiple, GPS satellites of the geolocation system 104. The positioning device 122 transmits the received signals to the processor 118. The processor 118 determines the spatial location for example, longitude and latitude coordinates, elevation/altitude, and the like) of the patient data gathering device 102 by analyzing the signals. The resulting spatial location information is transmitted to the server 108 via the network 106 by using a communication device 124, such as a cellular data transceiver or a Wi-Fi transceiver.

In some embodiments, the patient data gathering device 102 includes alternative or additional components and/or determines its position in other manners. For example, the position of the patient data gathering device 102 may be determined by cellular signal multilateration, Wi-Fi signal multilateration, accelerometer or gyroscope data, combinations thereof, and the like.

The patient data gathering devices 102 may include different components and/or operate in different manners. In some embodiments, for example, the patient data gathering device 102 includes separate processors (not shown) for analyzing signals received from the sensors 114 and the geolocation system 104. In some embodiments, the patient data gathering device 102 transmits the signals received from the geolocation system 104 to the server 108 and/or the remote device 110. The server 105 and/or the remote device 110 then determine the spatial location of the device 102 and optionally transmit the location information to the device 102.

In addition to transmitting location information, in some embodiments, the patient data gathering device 102 transmits stored device information (for example, the device's type, model number, serial number, device capabilities, assigned setting, such as an ambulance or hospital, and the like) and/or associated patient information (that is, information about the patient 116 to which the device 102 is assigned) to the server 108 via the network 106. Such patient information may include, for example, the patient's name, age, weight, height, medical history, past and/or real-time medical data obtained by the patient data gathering device 102, and the like. In some embodiments, the system 100 may use the ZOLL® RescueNet® Link system to transmit medical data obtained by the patient data gathering devices 102 to the server 108.

As described briefly above, the network 106 may be, for example, the Internet. As another example, the network 106 may be a "mesh" network in which the patient data gathering devices 102 define network nodes. In such a network, each of the devices 102 directly communicates with at least one other device 102 (for example, via NFC, Bluetooth, and the like). Further, at least one of the devices 102 directly communicates with the server 108 (for example, via NFC, Bluetooth, cellular data transmissions, Wi-Fi, and the like). Thus, the remainder of the devices 102 indirectly communicate with the server 108. Additional general aspects of mesh networks are described in Poor, Robert; WIRELESS MESH NETWORKS; Sensors (Feb. 1, 2003), which is incorporated herein by reference.

In one aspect of the present systems and methods, a mesh network may be employed if some of the devices 102 do not have, for example, cellular or Wi-Fi capabilities or if cellular or Wi-Fi service is not available to some of the devices 102. In some embodiments, each device 102 may analyze the location information transmitted by other devices 102 to determine, for example, the nearest adjacent device 102. Thus, each device 102 may then directly communicate with only the nearest adjacent device 102 to conserve power. In some embodiments, each device 102 may analyze the location information transmitted by other devices 102 to determine, for example, the shortest path for communicating with the server 108.

The server 108 receives information from the various patient data gathering devices 102. In some embodiments, a database 126 in communication with the server 108 stores device information (for example, device types, model numbers, serial numbers, device capabilities, assigned setting, and the like). The server 108 associates the appropriate device information with a device's location upon receiving location information and device identification (for example, the device's serial number or the like). Similarly, in some embodiments the database 126 stores patient information (for example, the patient's age, weight, height, medical history, and the like). The server 108 associates the appropriate patient information with a device's location upon receiving location information and patient identification (for example, the patient's name or the like).

Figure 2:
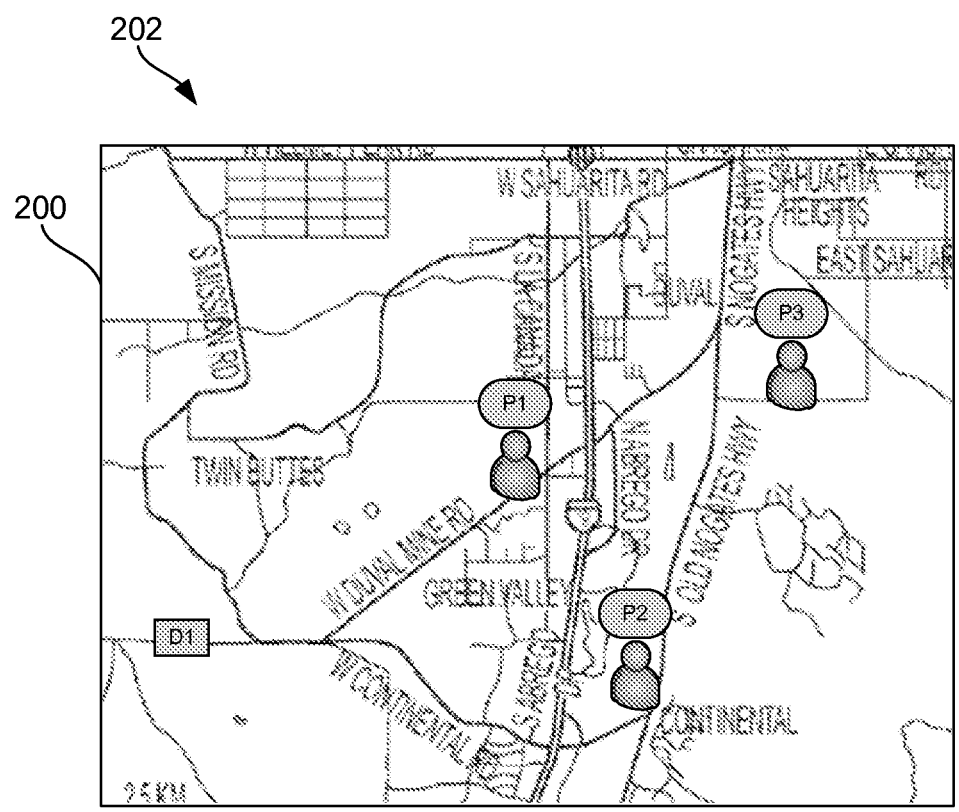
FIG. 2 illustrates an exemplary device/patient map created according to embodiments of the present invention.

Turning now to FIG. 2, the database 126 also stores electronic maps of various areas (for example, states, cities, ZIP codes, and the like). Upon receiving location information from one or more of the devices 102, the server 108 selects a map 200 including each of the locations. The server 108 uses the map 200 and the location information to create an aggregated device/patient map 202. Such a map 202 includes one or more unassigned device icons (for example, D1) and/or assigned device/patient icons (for example, P1) disposed on the map 202 according to the associated location information.

In some embodiments, the device/patient map 202 includes a list of the unassigned and/or assigned patient data gathering devices 102. Such a list may include, for example, arbitrary device and/or device/patient identifiers (such as D1, P1, and the like), device information (such as the type of device, model number, serial number, device capabilities, and the like), patient information (such as the patient's name, age, weight, height, medical history, and the like), spatial locations (such as longitude and latitude coordinates, elevation/altitude, and the like), distances from a particular facility (such as a nearby hospital), combinations thereof, and the like.

The device and patient icons may take various forms. In some embodiments, for example, the device icons may include a basic shape (such as a rectangle) and arbitrarily assigned distinguishing indicia (such as the term "D1" as shown in FIG. 2). As another example, each patient icon may include a general depiction of a patient (such as shapes representing the head and torso of a person as shown in FIG. 2) and arbitrarily assigned distinguishing indicia (such as the terms "P1", "P2", and "P3" as shown in FIG. 2). As another example, each patient icon may include the associated patient's name or initials.

In some embodiments, the patient icons may take different forms to provide an indication of a patient's medical condition. In some embodiments, the patient icons may include different colors to represent a patient's condition. For example, a green patient icon may represent a patient in stable condition, and a red patient icon may represent a patient in critical condition.

The server 108 transmits the device/patient map 202 to the remote device 110 for presentation on the remote device's display 128. The remote device 110 may be, for example, a desktop computer, a notebook computer, a tablet computer, a mobile telephone, or the like. In some embodiments, the server 108 transmits the same or different device/patient maps 202 to multiple remote devices 110.

In some embodiments, the system user 112 may manipulate the remote device 110 (for example, using a mouse, a keyboard, a touch-sensitive display, and the like) to select a specific area (for example, a city, ZIP code, and the like) for device and patient monitoring. In some embodiments, the remote device 110 may be assigned to continuously monitor a particular area (for example, a city, ZIP code, and the like). In this case, the system 100 may automatically and continuously update the locations of the unassigned and/or assigned patient data gathering devices 102 in the area.

In some embodiments, the system user 112 may manipulate the remote device 110 to interact with the device/patient map 202. For example, the system user 112 may pan or zoom the device/patient map 202 to depict different areas. As another example, the system user 112 may selectively show or hide landmarks (for example, roads, buildings, bodies of water, and the like) on the map 202. In latter case, the map 202 simply includes device and/or patient icons disposed at appropriate locations relative to each other.

Figure 3:
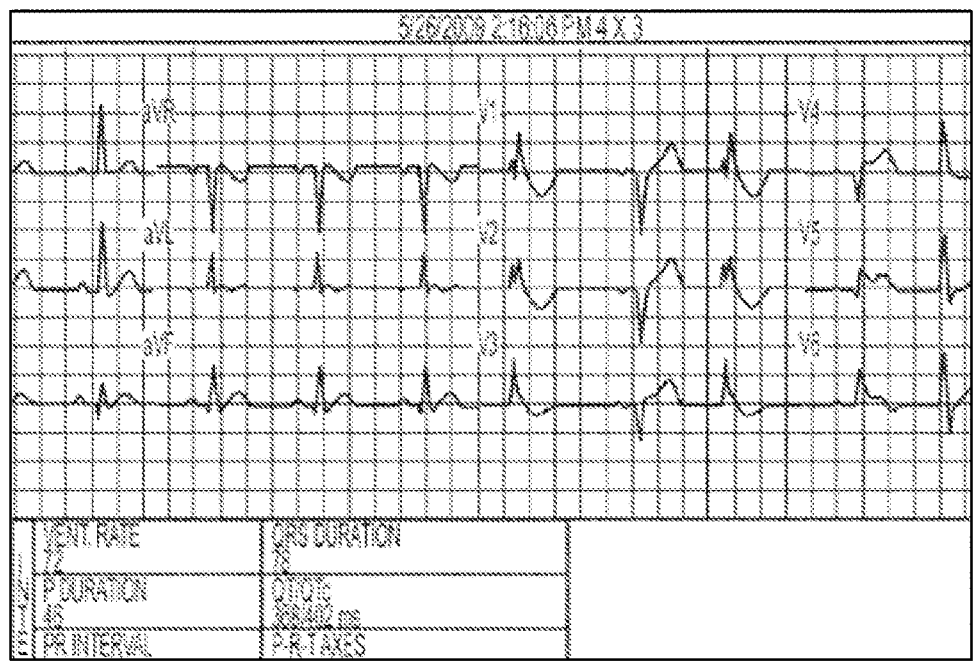
FIG. 3 illustrates an exemplary image displayed on a patient data gathering device and transmitted to a remote device according to embodiments of the present invention.

In some embodiments, the system user 112 may manipulate the remote device 110 to interact with the device and patient icons. For example, selecting one of the patient icons on the map 202 may cause the remote device's display 128 to present additional patient information. Such information may include, for example, the patient's name, age, weight, height, medical history, past and/or real-time medical data obtained by the patient data gathering device 102, and the like. As another example, selecting one of the patient icons may cause the remote device's display 128 to replicate the image presented on the display 120 of the associated patient data gathering device 102. For example, the display 128 may present an EGG 300 and other medical data as shown in FIG. 3. As yet another example, the display 128 may present real-time medical data obtained by the patient data gathering device 102, and/or the system user may enter a previous time (for example, an earlier date) from which medical data is to be presented.

In some embodiments, the remote device 110 may present information received from the patient data gathering devices 102 in any of the manners described in US Pat. App. Pub. 2011/0172550, which is incorporated herein by reference.

In some embodiments, the system user 112 may manipulate the remote device 110 to add further information to the device/patient map 202. For example, the system user 112 may enter information pertaining to a reported emergency (such as the patient's name, location, medical condition, and the like) to the remote device 110. If the information includes the patient's location, the system 100 may add a patient icon to the appropriate location on the device/patient map 202. Similarly, the system user 112 may enter information pertaining to the location of available resources (for example, ambulances lacking patient data gathering devices 102) or the system 100 may automatically incorporate vehicle location information received from, for example, the ZOLL® RescueNet® Navigator system. Thus, the system 100 may determine the nearest available resources and/or unassigned devices 102 to a reported emergency.

Figure 4:
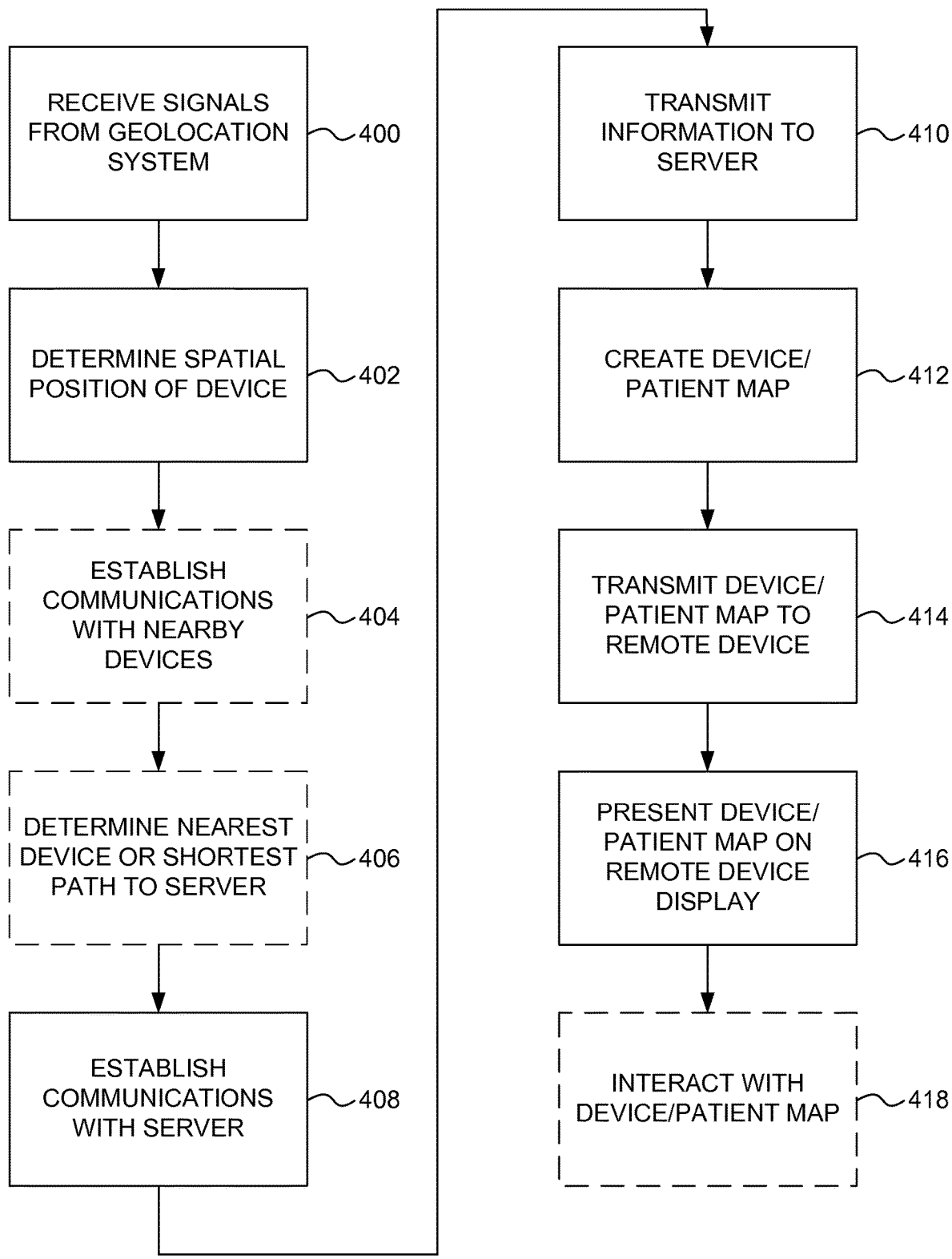
FIG. 4 illustrates an exemplary method for determining and displaying the spatial location of a patient data gathering device according to embodiments of the present invention.

Turning to FIG. 4, an exemplary method for determining and displaying the spatial location of a patient data gathering device 102 according to one embodiment of the invention is as follows. The method begins at step 400 by receiving signals from the geolocation system 104. At step 402, the device 102 analyzes the received signals to determine its spatial position. Optionally, the device 102 then establishes communications with nearby devices 102 at step 404. In some cases, the device 102 receives and analyzes position information from the other devices 102 to determine the nearest device 102 at step 406. Alternatively, the device 102 receives and analyzes position information from the other devices 102 to determine the shortest path for communicating with the server 108 at step 406. At step 408, the device 102 establishes communications (directly or indirectly) with the server 108 via the network 106. The device 102 transmits location information, device information, and patient information to the server 108 at step 410. At step 412, the server 108 creates a map including a device/patient icon disposed according to the location information. The server 108 then transmits the device/patient map 202 to the remote device 110 at step 414. At step 416, the remote device 110 presents the device/patient map 202 on its display 128. Optionally, the system user 112 manipulates the remote device 110 to interact with the device/patient map at step 418.

Figure 5:
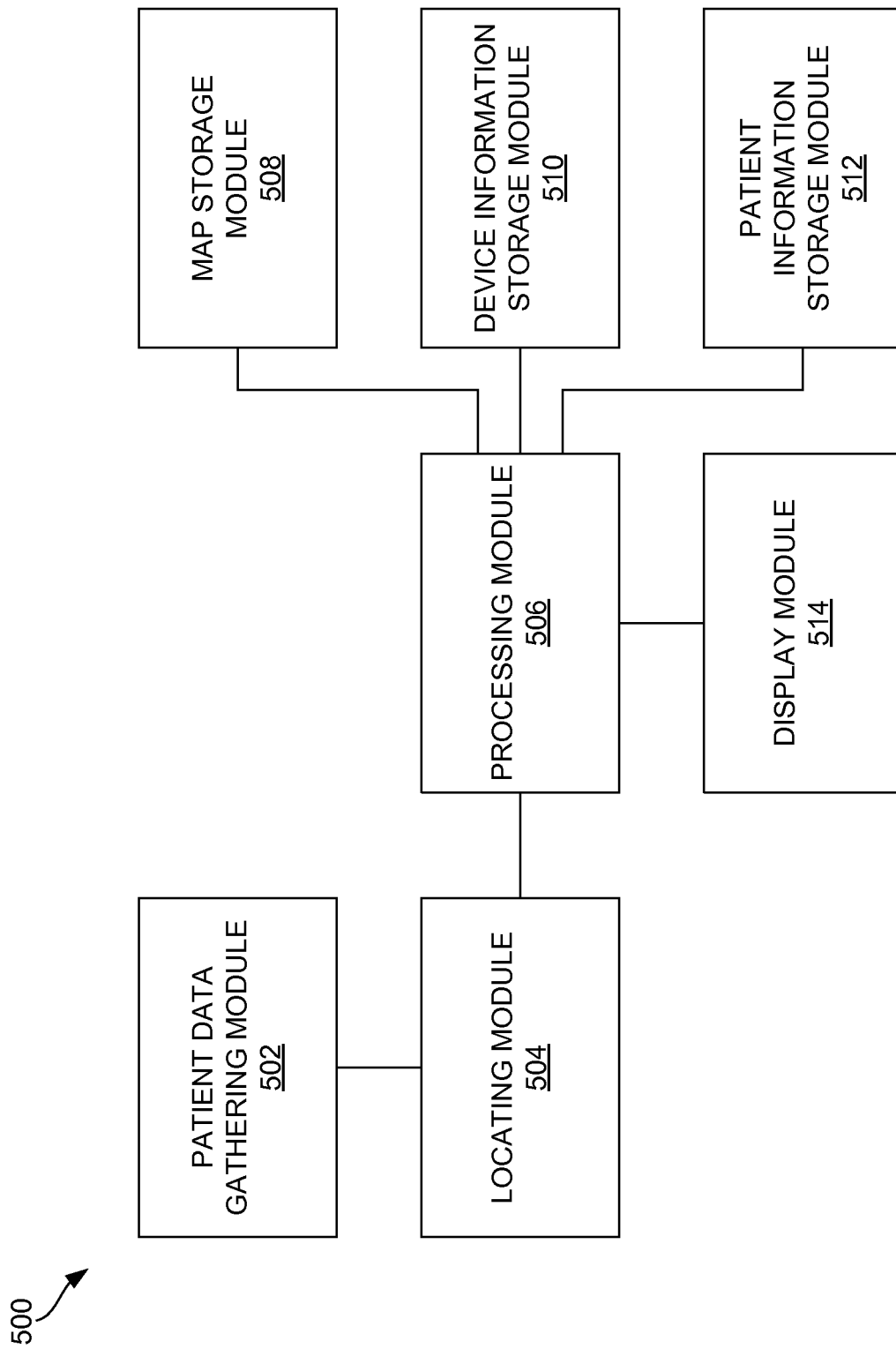
FIG. 5 illustrates a system overview for determining and displaying the spatial location of one or more patient data gathering devices according to embodiments of the present invention.

FIG. 5 illustrates a system 500 overview for determining and displaying the spatial location of one or more patient data gathering devices according to embodiments of the present invention. The system 500 includes a patient data gathering module 502 in communication with a locating module 504. The locating module 504 receives signals from a geolocation system and is in communication with a processing module 506. The processing module 506 is also in communication with a map storage module 508, a device information storage module 510, and a patient information storage module 512. The processing module 506 uses information received from the locating module 504, the map storage module 508, the device information storage module 510, and the patient information storage module 512 to create an interactive device/patient map. The processing module 506 is in communication with a display module 514 for presenting the device/patient map to a system user.

While the system 500 is described as having an ability to communicate with a server 108 over a network, system 500 may alternatively be included on a local device or a group of local devices for example patient data gathering device 102), or distributed across two or more local devices, which may operate in a similar manner without the involvement of a central server 108. As such, a map may be generated showing devices within a certain radius, for example 30 feet, 50 feet, 100 feet, 1000 feet, a mile, and the like, even without the involvement of a server 108 and/or a database 126 containing maps. Maps of local geographic or political features may be stored locally on the device on which the map is generated, and/or locally on device 102. Alternatively, even without any map overlay features, a map may be generated similar to that of FIG. 2, but showing only icons along with information about a relative location of the mapped devices 102, for example with respect to the device on which the map is generated or some other reference device. Such relative location information may permit rapid location of patient data gathering devices 102 in the field. The relative location information may include, for example, a legend indicating relative distance between icons, or distance information provided as a segment between icons with a textual distance identifier. According to some embodiments, the locating module 504 and the processing module 506 permit an icon to be selected from a map or a list of devices in order to activate a locating process, in which the user is provided with a directional and/or distance indicator to assist a mobile user in finding the particular device 102 represented by the icon.

In additional to two-dimensional maps, such as the map of FIG. 2, the system 100 may also permit three-dimensional location, for example by providing the device's 102 geographic coordinates as well as altitude and/or elevation. This may assist a user in locating one or more devices 102 on different levels of a multi-level building, and/or at different elevations of a hillside or ravine, and may be accomplished for example using GPS data. Such a function may also be particularly useful in a mass casualty situation.

In addition to locating devices 102 when devices 102 are in use (and thereby locating the patients with which the devices 10 are associated), the system 100 may also be configured to locate devices 102 in a similar manner for inventory, planning, and/or event review. For example, the system user 112, which may be a supervisor of an ambulance crew, may use the information from positioning devices 122 to determine how many devices 102 are deployed in the field and their current locations, in order to make possible real-location decisions. An ambulance crew may use such location information to determine whether the location of any devices 102 for which it is responsible matches with a location of their vehicle (e.g. to determine if any devices 102 have been left behind in an emergency response). Also, the device's 102 location information may be recorded along with other patient information, to permit a person later reviewing the medical incident data to know where the actual device 102 was located throughout the emergency response, as distinct from the location of the vehicle which was used to respond.

Systems and methods according to the present invention may be used in various situations. For example, the systems and methods may be used in mass casualty situations to locate both assigned and unassigned patient data gathering devices 102 in a particular area (for example, a city, a ZIP code, and the like). This facilitates assigning patient data gathering devices 102 to nearby patients. Further, this facilitates locating assigned patient data gathering devices 102 and, thus, the associated patients. As described above, in some embodiments, the patient icons indicate the medical condition of a patient (for example, by using various colors). Thus, the systems and methods may facilitate determining a chronological order for deployment of further resources (for example, air lift services, ambulance services, and the like). For example, further resources may be first deployed to relatively critical patients and then to relatively stable patients. Similarly, in some embodiments, the present systems and methods can be used to recognize assignment of a relatively simple data gathering device 102 (for example, a basic life support device employed by fire services) to a patient. Subsequently and if warranted by the patient's condition, a relatively sophisticated data gathering device 102 (for example, an advanced life support device employed by ambulance services) can be directed to the patient.

In the above situations, the system users 112 could be EMS dispatchers. The dispatchers could direct personnel and resources to appropriate locations according to information provided by the present systems and methods. Alternatively or additionally, the system users 112 could be ambulatory personnel (such as ambulance personnel, fire department personnel, and the like) and the remote device 110 could be a portable device (such as a notebook computer, a tablet computer, and the like). Thus, the ambulatory personnel could determine, for example, the location and identity of nearby patients by using the remote device 110.

In various situations the device's 102 location may be used to approximately determine the location of resources (such as air lift services, ambulance services, and the like) and/or personnel (such as ambulance personnel, fire department personnel, and the like) employing the device 102.

As another example and particularly if the patient data gathering devices 102 are wearable cardioverter defibrillators, the present systems and methods may be used in hospital settings to monitor the location and movement of one or more ambulatory patients.

As yet another example, the present systems and methods may be used in various settings to identify nearby storage and/or maintenance locations for the devices 102 (for example, a storage area in a hospital). The systems and methods may also provide directions for moving the devices 102 to nearby or previously assigned storage and/or maintenance locations.

Figure 6:
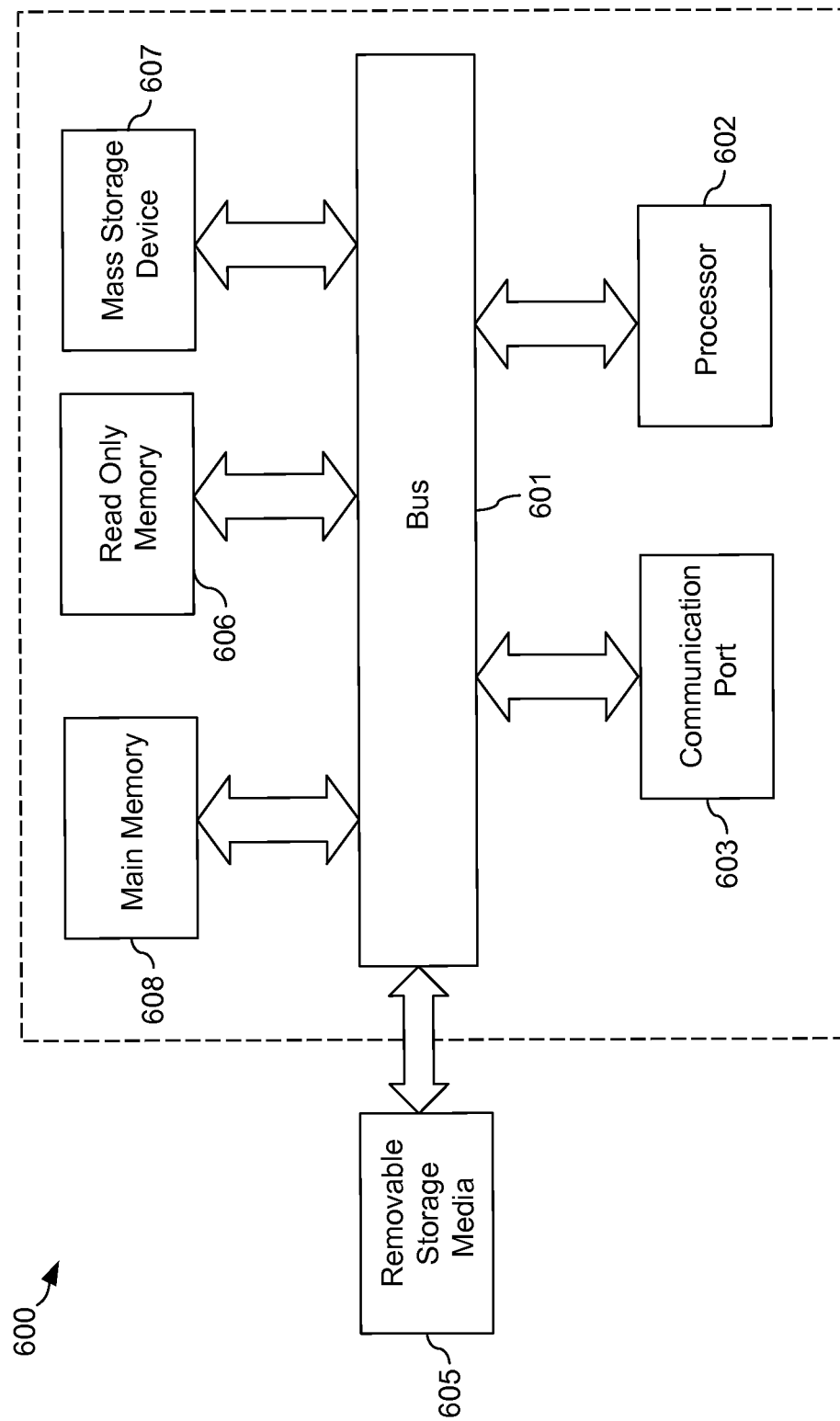
FIG. 6 illustrates an exemplary computer system according to embodiments of the present invention.

FIG. 6 is an exemplary computer system 600 with which embodiments of the present invention may be utilized. According to the present example, the computer system includes a bus 601, at least one processor 602, at least one communication port 603, a main memory 608, a removable storage media 605, a read only memory 606, and a mass storage 607.

Processor(s) 602 can be any known processor, such as an Intel® Itanium® or Itanium 2® processor(s), or AMD® Opteron® or Athlon MP® processor(s), or Motorola® lines of processors. Communication port(s) 603 can be any of an RS-232 port for use with a modem based dialup connection, a 10/100 Ethernet port, a Gigabit port using copper or fiber, or a wireless communication port, for example. Communication port(s) 603 may be chosen depending on a network such a Local Area Network (LAN), Wide Area Network (WAN), or any network to which the computer system 600 connects. Main memory 608 can be Random Access Memory (RAM), or any other dynamic storage device(s) commonly known to one of ordinary skill in the art. Read only memory 606 can be any static storage device(s) such as Programmable Read Only Memory (PROM) chips for storing static information such as instructions for processor 602, for example.

Mass storage 607 can be used to store information and instructions. For example, hard disks such as the Adaptec® family of SCSI drives, an optical disc, an array of disks such as RAID (for example, the Adaptec family of RAID drives), or any other mass storage devices may be used, for example. Bus 601 communicably couples processor(s) 602 with the other memory, storage and communication blocks. Bus 601 can be a PCI/PCI-X or SCSI based system bus depending on the storage devices used, for example. Removable storage media 605 can be any kind of external hard-drives, floppy drives, flash drives, IOMEGA® Zip Drives, Compact Disc Read Only Memory (CD-ROM), Compact Disc Re-Writable (CD-RW), or Digital Video Disk-Read Only Memory (DVD-ROM), for example.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A medical equipment system comprising:
    a plurality of patient data gathering devices, each patient gathering device of the plurality of patient data gathering devices configured to connect to a respective patient and to transmit patient data gathering device location information and patient data gathering device information comprising real-time patient medical data while connected to the respective patient and gathering the real-time patient medical data from the respective patient; and
    a mobile computing device comprising:
        a display, and
        a processor, a memory comprising program instructions, and associated circuitry, the processor configured to execute the program instructions to:
            receive the real-time patient medical data transmitted from the plurality of patient data gathering devices while the plurality of patient data gathering devices are connected to respective patients and gathering the real-time patient medical data from the respective patients,
            receive the patient data gathering device location information for the plurality of patient data gathering devices, the patient data gathering device location information being indicative of one or more patient data gathering device locations in an assigned monitoring area corresponding to the mobile computing device,
            provide the patient data gathering device location information at the display,
            capture a user selection of at least one patient data gathering device of the plurality of patient data gathering devices based on the provided patient data gathering device location information, and
            provide the patient data gathering device information at the display based on the user selection, the patient data gathering device information comprising the real-time patient medical data from the at least one patient data gathering device, wherein the memory of the mobile computing device further comprises processor executable program instructions for a reallocation decision for the patients or a reallocation decision for one or more of the patient data gathering devices, and program instructions for displaying, wherein the reallocation decision for the patients or the reallocation decision for the one or more patient gathering devices is displayed on the display.

2. The system of claim 1 wherein the patient data gathering device information comprises one or more of a patient name, age, weight, height, medical history, and historical medical data.

3. The system of claim 2 wherein the historical medical data and the real-time patient medical data comprise one or more of heart rate, blood pressure, temperature, respiration rate, blood oxygen level, end-tidal carbon dioxide level, pulmonary function, blood glucose level, an electrocardiograph.

4. The system of claim 3 wherein the processor is configured to capture at least one of a user entered time and date and provide the historical medical data corresponding to the at least one of the user entered time and date.

5. The system of claim 1 wherein the processor is configured to automatically receive updated patient data gathering device location information for the assigned monitoring area.

6. The system of claim 1 wherein the display is a touch-sensitive display.

7. The system of claim 1 wherein the processor is configured to capture a user selection of the assigned monitoring area.

8. The system of claim 1 wherein the processor is configured to provide the patient data gathering device location information on a map.

9. The system of claim 8 wherein the map comprises one or more selectable icons corresponding to the one or more patient data gathering device locations.

10. The system of claim 8 wherein the one or more patient data gathering device locations are locations in proximity to the mobile computing device.

11. The system of claim 8 wherein the map includes depictions of landmarks proximate to the one or more patient data gathering device locations.

12. The system of claim 8 wherein the map comprises three-dimensional patient data gathering device location information.

13. The system of claim 12 wherein the three-dimensional patient data gathering device location information is indicative of the one or more patient data gathering device locations within a multi-level building.

14. The system of claim 13 wherein the patient data gathering device location information comprises navigation instructions that enable a user of the mobile computing device to locate the at least one patient data gathering device within the multi-level building.

15. The system of claim 12 wherein the three-dimensional patient data gathering device location information comprises geographic longitude and latitude coordinates and comprises elevation or altitude.

16. The system of claim 8 wherein the map comprises patient icons for patients associated with the plurality of patient data gathering devices.

17. The system of claim 16 wherein the patient icons may include patient identification.

18. The system of claim 16 wherein the patient icons may include one or more colors indicative of a patient condition.

19. The system of claim 16 wherein the processor is configured to:
  capture a patient's name and a patient's location via user input, and
  add a patient icon to the map based on the patient's location.

20. The system of claim 8 wherein the processor is configured to pan or zoom the map provided at the display in response to user input.

21. The system of claim 1 wherein the patient data gathering device location information comprises navigation instructions that direct a user of the mobile computing device to the at least one patient data gathering device.

22. The system of claim 1 wherein the patient data gathering device information comprises a list of patient data gathering devices.

23. The system of claim 1 wherein the patient data gathering device information comprises one or more of device capabilities and device settings.

24. The system of claim 1 wherein the patient data gathering device information comprises address information comprising one or more of a state, a city, and a ZIP code.

25. The system of claim 1 wherein the patient data gathering device information comprises one or more of a device type, a serial number, a model number, and a physical location description for one or more of the plurality of patient data gathering devices.

26. The system of claim 1 wherein the processor is configured to control the display to replicate an image from a patient data gathering device.

27. The system of claim 1 wherein the patient data gathering device location information is indicative of a spatial proximity of a first defibrillator to a second defibrillator.

28. The system of claim 1 wherein the plurality of patient data gathering devices comprises at least one defibrillator and the patient data gathering device location information is indicative of a spatial proximity between the at least one defibrillator and the mobile computing device.

29. The system of claim 1 wherein the plurality of patient data gathering devices comprises at least one of defibrillators, automatic external defibrillators, or wearable cardioverter defibrillators, and combinations thereof.

30. The system of claim 1 wherein the patient data gathering device location information is indicative of one or more of a location and movement for an ambulatory patient associated with at least one of the plurality of patient data gathering devices.

31. The system of claim 1 wherein the processor is configured to receive the patient data gathering device information and the patient data gathering device location information from a server database.

32. The system of claim 1 wherein the processor is configured to receive the patient data gathering device information and the patient data gathering device location information from the memory.

33. The system of claim 1 wherein the mobile computing device is one of a tablet computer, a mobile telephone, or a notebook computer.

34. A medical equipment system comprising:
  a plurality of patient data gathering devices, each configured to connect to a patient and to transmit patient data gathering device location information and patient data gathering device information comprising real-time patient medical data while connected to the patient and gathering the real-time patient medical data from the patient; and
  a mobile computing device comprising:
    a display, and
    a processor, a memory, and associated circuitry, the processor configured to:
      receive the real-time patient medical data transmitted by each of the plurality of patient data gathering devices while connected to the patient and gathering the real-time patient medical data from the patient,
      receive the patient data gathering device location information for the plurality of patient data gathering devices, the patient data gathering device location information being indicative of one or more patient data gathering device locations in an assigned monitoring area corresponding to the mobile computing device,
      provide the patient data gathering device location information on a map at the display, wherein the map comprises three-dimensional patient gathering device location information and patient icons for patients associated with the plurality of patient data gathering devices,
      capture a user selection of at least one patient data gathering device of the plurality of patient data gathering devices based on the provided patient data gathering device location information, and
      provide the patient data gathering device information at the display based on the user selection, the patient data gathering device information comprising the real-time patient medical data from the at least one patient data gathering device.

35. The system of claim 34 wherein the patient data gathering device information comprises one or more of a patient name, age, weight, height, medical history, and historical medical data.

36. The system of claim 35 wherein the historical medical data and the real-time patient medical data comprise one or more of heart rate, blood pressure, temperature, respiration rate, blood oxygen level, end-tidal carbon dioxide level, pulmonary function, blood glucose level, an electrocardiograph.

37. The system of claim 36 wherein the processor is configured to capture at least one of a user entered time and date and provide the historical medical data corresponding to the at least one of the user entered time and date.

38. The system of claim 34 wherein the processor is configured to automatically receive updated patient data gathering device location information for the assigned monitoring area.

39. The system of claim 34 wherein the display is a touch-sensitive display.

40. The system of claim 34 wherein the processor is configured to capture a user selection of the assigned monitoring area.

41. The system of claim 34 wherein the map comprises one or more selectable icons corresponding to the one or more patient data gathering device locations.

42. The system of claim 34 wherein the one or more patient data gathering device locations are locations in proximity to the mobile computing device.

43. The system of claim 34 wherein the map includes depictions of landmarks proximate to the one or more patient data gathering device locations.

44. The system of claim 34 wherein the three-dimensional patient data gathering device location information is indicative of the one or more patient data gathering device locations within a multi-level building.

45. The system of claim 44 wherein the patient data gathering device location information comprises navigation instructions that enable a user of the mobile computing device to locate the at least one patient data gathering device within the multi-level building.

46. The system of claim 34 wherein the three-dimensional patient data gathering device location information comprises geographic longitude and latitude coordinates and comprises elevation or altitude.

47. The system of claim 34 wherein the patient icons may include one or more of patient identification and one or more colors indicative of a patient condition.

48. The system of claim 34 wherein the processor is configured to:
capture a patient's name and a patient's location via user input, and
add a patient icon to the map based on the patient's location.

49. The system of claim 34 wherein the processor is configured to pan or zoom the map provided at the display in response to user input.

50. The system of claim 34 wherein the patient data gathering device location information comprises navigation instructions that direct a user of the mobile computing device to the at least one patient data gathering device.

51. The system of claim 34 wherein the patient data gathering device information comprises one or more of a list of patient data gathering devices, address information, a physical location description, a device type, a serial number, a model number, device capabilities, and device settings.

52. The system of claim 34 wherein the processor is configured to control the display to replicate an image from a patient data gathering device.

53. The system of claim 34 wherein the plurality of patient data gathering devices comprises at least one defibrillator and the patient data gathering device location information is indicative of a spatial proximity between the at least one defibrillator and one or more of the mobile computing device and at least one other defibrillator.

54. The system of claim 34 wherein the plurality of patient data gathering devices comprises at least one of defibrillators, automatic external defibrillators, or wearable cardioverter defibrillators, and combinations thereof.

55. The system of claim 34 wherein the patient data gathering device location information is indicative of one or more of a location and movement for an ambulatory patient associated with at least one of the plurality of patient data gathering devices.

56. The system of claim 34 wherein the processor is configured to receive the patient data gathering device information and the patient data gathering device location information from a server database.

57. The system of claim 34 wherein the processor is configured to receive the patient data gathering device information and the patient data gathering device location information from the memory.

58. The system of claim 34 wherein the mobile computing device is one of a tablet computer, a mobile telephone, or a notebook computer.

* * * * *